(12) United States Patent
Kurup

(10) Patent No.: US 6,786,601 B1
(45) Date of Patent: Sep. 7, 2004

(54) METHOD OF CONVENIENTLY THWARTING INFANT AMBLYOPIA AFTER CATARACT REMOVAL

(76) Inventor: Shree Kumar Kurup, 1-142 Maplewood WMC Mailbox #513, Valhalla, NY (US) 10595

( * ) Notice: Subject to any disclaimer, the term of this patent is extended or adjusted under 35 U.S.C. 154(b) by 109 days.

(21) Appl. No.: 10/243,441

(22) Filed: Sep. 14, 2002

(51) Int. Cl.[7] .............. A61B 3/04; A61F 9/00
(52) U.S. Cl. .............. 351/230; 351/246; 2/15; D29/110
(58) Field of Search ............. 351/230, 246, 351/41, 57, 154, 161; 2/15, 426, 428; D29/110, 106–108; 54/80, 2; 602/41, 74, 61; 128/858, 898

(56) References Cited

U.S. PATENT DOCUMENTS

| | | | | |
|---|---|---|---|---|
| 4,582,401 A | * | 4/1986 | Grindle | 351/45 |
| 4,727,869 A | * | 3/1988 | Leonardi | 602/74 |
| 4,907,580 A | * | 3/1990 | Leonardi | 602/74 |
| 5,016,999 A | * | 5/1991 | Williams | 351/41 |
| 5,191,897 A | * | 3/1993 | Meshel | 600/558 |
| 5,949,514 A | * | 9/1999 | Wargon | 351/41 |
| 6,149,615 A | * | 11/2000 | Gallamore | 602/61 |
| 6,388,813 B1 | * | 5/2002 | Wilson et al. | 359/630 |
| D466,610 S | * | 12/2002 | Ashton et al. | D24/189 |
| 2002/0144336 A1 | * | 10/2002 | Montague | 2/452 |

* cited by examiner

Primary Examiner—Brian L. Casler
Assistant Examiner—John R Sanders
(74) Attorney, Agent, or Firm—Robert Nathans

(57) ABSTRACT

A flexible transparent mask having a vision blocking portion is positioned over the infant's "good" eye to prevent amblyopia and a large plastic corrective lens is positioned over the eye under correction, and is heat laminated to the mask during manufacture. Since the entire mask is mounted upon and removed from the infant's face in a single motion, separate application and removal of a corrective lens and a conventional patch is avoided for convenience. The mask avoids the cumbersome conventional removal, sterilization and reinsertion of a contact lens to prevent infection, or alternatively, the use of external eyeglasses which the child can peek around, unlike the preferred mask held close to the infant's face. Another embodiment uses a double-sided adhesive ring for affixing the lens over the infant's eye along with a separately applied eye patch over the "good" eye.

12 Claims, 1 Drawing Sheet

METHOD OF CONVENIENTLY THWARTING INFANT AMBLYOPIA AFTER CATARACT REMOVAL

BACKGROUND OF THE INVENTION

The present invention relates to the field of ocular surgery.

Deprivation of visual stimulus before the age of about eight, due to cataract removal or other causes such as blood in front of the eye, asymmetric need for glasses over one eye due to for example shortsightedness, or any other condition that blocks the center of the visual axis, can lead to a condition called amblyopia (am-blee-oh-pee-ah) or "lazy eye". In this situation, the eye itself is intact and has the potential for functioning but the proper brain connection is withered due to the period in which the eye was denied light exposure and visual stimuli and permanent serious impairment of vision can result. For a discussion of this well known condition, reference may be made to U.S. Pat. No. 5,900,921 to Min and U.S. Pat. No. 6,149,615.

Infants after birth can require ocular surgery involving removal of a vision blocking condition such as a cataract in the baby's eye. The conventional procedure involves replacing the removed natural lens bearing the cataract, with infant configured external eyeglasses or alternatively, with a contact lens so that the infant can focus upon objects and use the "bad" eye. The other "good" eye is covered with an eye patch to force the infant to use the operated on eye in order to prevent amblyopia.

In the common case of cataract removal, a strong lens is positioned over the operated on, now lens-less eye, to enable the infant to focus upon objects and thus maintain visual stimulation to thwart amblyopia, while applying a patch or eye-drops, rendering vision fuzzy, to occlude the good eye and accordingly force the infant to use the operated on eye. Unlike the situation where adults wear glasses to restore vision, certain problems arise when the above mentioned external eyeglasses are supplied for use with an infant, as they are often removed by the infant who is annoyed by them or shifted in position by the infant so that he can peek around the lens. This often results in the use of contact lenses. However, contact lenses are a nuisance to periodically remove and clean to prevent infection in the case of adult usage, and to remove and clean the contact lenses worn by an infant, thrashing about, can be even more aggravating. Injury to the child's eye is also possible under these circumstances. Hence, a solution to these problems is desired.

SUMMARY OF PREFERRED EMBODIMENTS OF THE INVENTION

In order to more conveniently thwart infant amblyopia, the presently preferred method of the invention includes the steps of providing a flexible visually clear thermoplastic mask-like sheet member having an opaque vision blocking area to be positioned over the infant's "good" eye and a large plastic corrective lens to be positioned in place over the infant's "bad" eye under correction. During manufacture of the mask, the large plastic lens can be readily heat laminated to the transparent flexible thermo-plastic mask-like sheet member. The mask can be mounted upon the child's face in one step since both the large plastic lens and light blocking substitute for the patch are both part of the mask. This is in contrast with applying the external eyeglasses or contact lens in one step and a separate patch in another step.

In accordance with another method of carrying out the invention, a thin annular plastic lens mounting ring is provided, having an upper adhesive surface and a lower adhesive surface. Outer lower peripheral portions of the plastic lens overlap and become affixed to inner rim upper adhesive portions of the annular ring during manufacture of the lens unit. Upon use of the ring unit, the lower adhesive portions of the ring are manually affixed to facial portions of the infant surrounding the eye under correction. A separate strapless adhesive bearing eye patch is concurrently manually applied to cover the good eye to thwart amblyopia. Thus, the large plastic lens Accordingly, in both embodiments, the plastic lens is larger than the largest eye of most infants subject to treatment, to remove the need for lens size fitting. The large plastic lens directly clings to the infant's face over the eye to preclude the "peek around" tendency of external eyeglasses or precludes the need for inconvenient contact lens insertion and removal.

BRIEF DESCRIPTION OF THE DRAWINGS

Other features and advantages of the invention will become apparent upon study of the following detailed description, taken in conjunction with the drawings in which.

DETAILED DESCRIPTION OF PREFERRED EMBODIMENTS OF THE INVENTION

Figure 1:
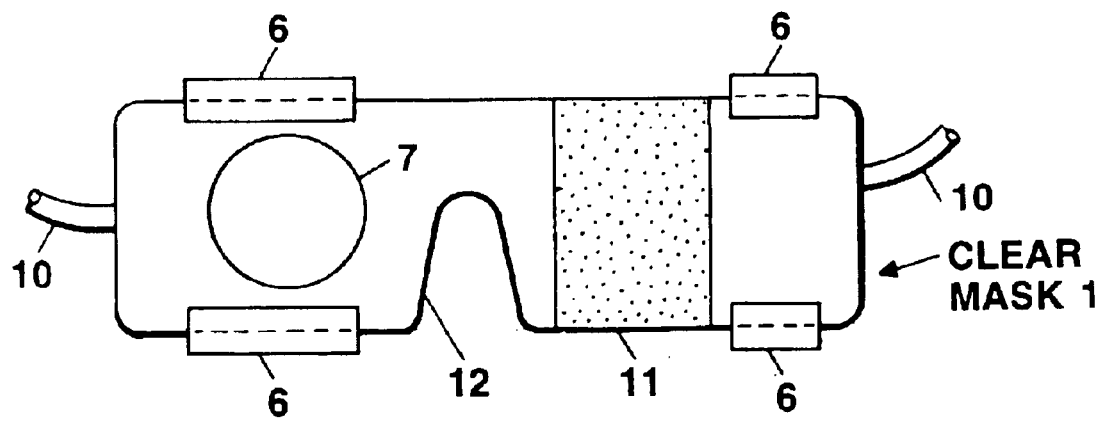
FIGS. 1 and 2 disclose front and side views respectively, of a mask applied over the face of the infant in order to attain the aims and advantages of the invention.
Figure 2:
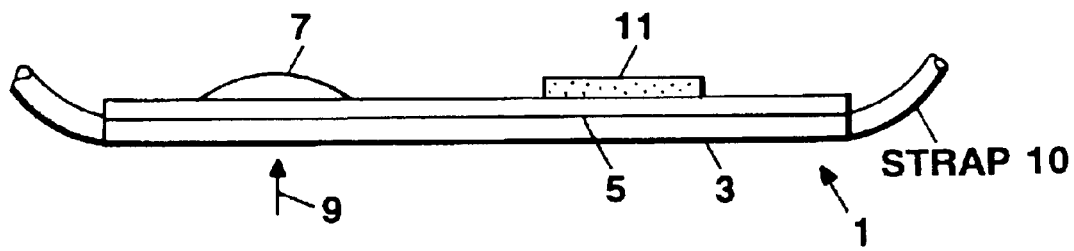

As shown in FIGS. 1 and 2, a flexible clear transparent plastic facial mask 1 is provided having a "Mylar" polyethylene terepthalate base layer 3 and a transparent polyethylene or polyolefin heat activatable layer 5 integral with layer 3. These clear structured two-layered transparent plastic sheets are widely available in the commercial market for use in making clear laminated data bearing cards such as ID cards or driver's licenses, and the preferred thickness for use herein are sheets having a thickness of about two to three mils for good flexibility. See U.S. Pat. No. 5,042,843 to Kuhns et al. During manufacturing of the clear mask 1, a large diameter non-breakable plastic lens 7 is laminated by the application of heat and pressure as indicated by arrow 9 to the mask 1 by virtue of the heat activatable layer 5.

Transparent layer 5 will not interfere with clear vision. This is a simple manufacturing process that can be readily performed by a small platen press or even by an ordinary kitchen iron. The plastic lens 7 has a large diameter suitable for covering small or large eye dimensions, and has a high power to function as the infant's natural lens removed by the surgeon. The use of an ordinary water-based acrylic optically clear adhesive for plastic lens lamination to substrates, also is disclosed in U.S. Pat. No. 6,388,813 to Wilson et al.

Vision blocking means 11 on the mask can consist of a dark adhesive tape adhered to the transparent mask or an opaque coating, and functions to force the infant to use the "bad" eye under treatment, because it blocks light from reaching the "good" eye to prevent amblyopia of the "bad" operated eye positioned under high power plastic lens 7 as discussed above. The plastic mask can be affixed to the infant's face via adhesive tape segments 6 and/or elastic straps 10 that can encircle the child's head. Cutout portion 12 can be provided in the mask to accommodate the nose of the infant.

Figure 3:
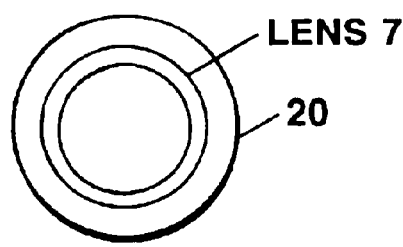
FIGS. 3 and 4 disclose front and side views of a lens unit that is applied over the infant's eye under correction in order to attain the aims and advantages of the invention.
Figure 4:
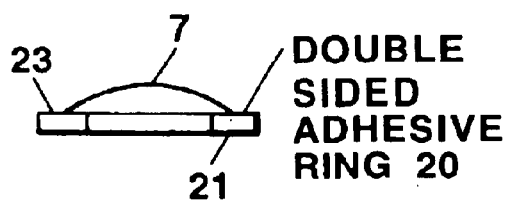

An alternative embodiment is illustrated in FIGS. 3 and 4 wherein a coupling member is provided, comprising a thin annular ring 20 having an upper adhesive surface 23 and a lower adhesive surface 21. The double-sided adhesive annular ring can comprise ordinary adhesive bandage material and can be used to affix plastic lens 7 to the face of the infant.

More specifically, extreme thin peripheral rim portions of plastic lens 7 are affixed to upper annular adhesive surface 23 of annular ring member 20 upon manufacture of the lens unit, while lower portions 21 of the ring member during use of the lens unit are affixed to facial portions of the infant surrounding the operated upon eye.

However, unlike the mask embodiment of FIGS. 1 and 2, a separate conventional light blocking eye patch has to be manually positioned over the "good" eye. Patents disclosing various types of eye patches are listed in column 1 of U.S. Pat. No. 6,149,615. However, the infant can remove eye patches with straps to one side to use his good eye to see around the patch. Also, repeated application and removal of the aforesaid adhesive lens bearing ring over the infant's face can result in the need to replace the ring as the adhesive loses its gripping ability. This can either require a completely new plastic lens/adhesive ring member or require that the used lens be carefully remounted upon a fresh adhesive ring, and such careful lens edge alignment with the inner ring portion can be tedious. For these reasons, the unitary mask embodiment of FIGS. 1 and 2 is presently preferred.

As variations in the described embodiments will occur to workers in the art, the scope of the invention is to be limited solely by the terms of the following claims and art recognized equivalents. For example, the term "large plastic lens" is intended to include a lens made of any non-breakable transparent material and includes any lens that tends to be somewhat larger in diameter than the average infant's eye in order to avoid lens sizing or fitting procedures employed upon proscribing eye-glasses for adults. The annular coupling member need not completely surround the lens periphery, but could be "C-shaped" so as to make room for the infant's nose. Rather than heat laminating the lens to the flexible thermoplastic mask-like sheet as described, the mask member and lens could be injection molded as a single piece during manufacture.

I claim:

1. Method of thwarting infant amblyopia of a good eye while simplifying correction of vision of an eye under correction following medical treatment comprising the steps of:
   (a) applying a vision blocking means over said good eye;
   (b) providing a non-breakable lens; and
   (c) causing said non-breakable lens to cling to facial portions of said infant adjacent said eye under correction;
   (d) and wherein step (c) comprises mounting a mask having said non-breakable lens thereon, upon facial portions of said infant, said mask being configured to cover said good eye and block light therefrom.

2. The method of claim 1 wherein said mask is at least partially held in position by an elastic strap.

3. The method of claim 1 wherein step (d) includes positioning pressure sensitive adhesive means between said mask and facial portions of said infant.

4. The method of claim 2 wherein step (d) includes positioning pressure sensitive adhesive means between said mask and facial portions of said infant.

5. Method of thwarting infant amblyopia of a good eye while simplifying correction of vision of an eye under correction following medical treatment comprising the steps of:
   (a) applying a vision blocking means over said good eye;
   (b) providing a large plastic lens; and
   (c) mounting said large plastic lens over said eye under correction in a manner causing said plastic lens to cling to facial portions of said infant adjacent said eye under correction; and
   (d) wherein step (c) includes mounting a mask having said large plastic lens thereon, upon facial portions of said infant, said mask being configured to cover said good eye and block light therefrom.

6. The method of claim 5 wherein said mask is at least partially held in position by an elastic strap.

7. The method of claim 5 wherein step (d) includes positioning pressure sensitive adhesive means between said mask and facial portions of said infant.

8. The method of claim 6 wherein step (d) includes positioning pressure sensitive adhesive means between said mask and facial portions of said infant.

9. Method of thwarting infant amblyopia of a good eye while simplifying correction of vision of an eye under correction following medical treatment comprising the steps of:
   (a) providing a flexible thermo-plastic mask-like member having vision blocking means to be positioned over said good eye and a large plastic corrective lens to be positioned overlaying said eye under correction, and wherein said large plastic lens is heat laminated to said flexible thermo-plastic mask-like sheet member; and
   (b) positioning said mask-like member in contact with an infant's face in a manner to block light from visually stimulating said good eye while exposing the eye under correction to light passing through said large plastic corrective lens.

10. The method of claim 9 wherein step (b) is carried out by taping edge portions of said mask-like member to facial portions of said infant.

11. The method of claim 9 wherein said mask is at least partially held in position by an elastic strap.

12. The method of claim 10 wherein said mask is at least partially held in position by an elastic strap.

* * * * *